United States Patent [19]
Strowe

[11] Patent Number: 5,989,240
[45] Date of Patent: Nov. 23, 1999

[54] ADAPTOR FOR MOUNTING A FLUID HANDLING DEVICE ON A CATHETER TUBING

[75] Inventor: Robert J. Strowe, Ramsey, N.J.

[73] Assignee: Becton, Dickson and Company, Franklin Lakes, N.J.

[21] Appl. No.: 09/032,157

[22] Filed: Feb. 27, 1998

[51] Int. Cl.⁶ .................................................. A61M 25/16
[52] U.S. Cl. ........................... 604/533; 604/905; 285/81; 285/340
[58] Field of Search ................................... 604/240, 242, 604/243, 280, 283, 905, 533; 285/81, 308, 340

[56] References Cited

U.S. PATENT DOCUMENTS

| | | | |
|---|---|---|---|
| 4,013,310 | 3/1977 | Dye | 285/110 |
| 4,712,810 | 12/1987 | Pozzi | 285/93 |
| 4,842,592 | 6/1989 | Caggiani et al. | 604/283 |
| 5,053,015 | 10/1991 | Gross | 604/167 |
| 5,209,740 | 5/1993 | Bryant et al. | 604/243 |
| 5,226,898 | 7/1993 | Gross | 604/243 |
| 5,285,776 | 2/1994 | Bertram | 604/283 X |
| 5,312,337 | 5/1994 | Flaherty et al. | 604/93 |
| 5,312,375 | 5/1994 | Gurmarnik | 604/264 |
| 5,336,162 | 8/1994 | Palestrant | 604/167 |
| 5,336,313 | 8/1994 | Mollenauer et al. | 604/249 |
| 5,338,314 | 8/1994 | Ryan | 604/284 |
| 5,366,262 | 11/1994 | Couvreur | 285/340 |
| 5,405,340 | 4/1995 | Fageol et al. | 604/283 |
| 5,464,400 | 11/1995 | Collins | 604/283 |
| 5,507,732 | 4/1996 | McClure et al. | 604/280 |
| 5,584,820 | 12/1996 | Gurmarnik | 604/264 |
| 5,599,328 | 2/1997 | Stevens | 604/283 |
| 5,695,224 | 12/1997 | Grenier | 285/104 |
| 5,730,476 | 3/1998 | Gouda | 285/340 |

Primary Examiner—Corrine McDermott
Attorney, Agent, or Firm—Scott S. Servilla

[57] ABSTRACT

An adapter of the present invention useful for attaching a fluid handling device to a catheter includes a body having a proximal end, a distal end and an open passageway therethrough. The passageway includes a seat to receive the catheter and a cavity distal to the catheter seat. There is a gasket disposed in the cavity to form a substantially fluid tight seal about the catheter when the catheter is positioned on the catheter seat. The adapter further includes a retainer, disposed on the distal end of the body over the gasket with an opening therethrough that is substantially aligned with the passageway. The opening is sufficient to allow the catheter to pass through into the passageway to engage the gasket and the catheter seat. The retainer has a plurality of flexible projections into the opening that are sized and shaped to engage the catheter and be proximally deflected by the placement of the catheter on the catheter seat. There is a rotatable collar disposed over the retainer on the proximal end of the body, with an open port therethrough that is substantially aligned with the passageway to allow placement of the catheter into the passageway. The collar has a plurality of proximal protuberances disposed to engage the flexible projections and to prevent distal flexion of the flexible projections on the retainer when the collar is in a first position with respect to the body thus to retaining the catheter in the adapter for attachment to a fluid handling device. Additionally, the protuberances are disposed not to engage the flexible projections when the collar is rotated to a second position with respect to the body thereby to allow a distal flexion of the projections and a withdrawal of the catheter from the adapter.

18 Claims, 8 Drawing Sheets

ADAPTOR FOR MOUNTING A FLUID HANDLING DEVICE ON A CATHETER TUBING

FIELD OF INVENTION

The present invention is generally related to the field of catheters and more particularly to adapters for mounting a fluid handling device on a catheter tubing.

BACKGROUND

Catheters are elongate hollow tubes that are used to transmit fluids into or out of the body of a patient. Conventions followed for the devices described in this disclosure are that the term "proximal" is the direction away from the patient and toward the practitioner and the term "distal" refers to the direction toward the patient and away from the practitioner.

There are many types of catheters currently used in medical practice. Some catheters are sufficiently strong and rigid to be introduced by themselves, urinary catheters are examples of this type of catheter. Another catheter type is positioned on the outside of a sharp introducer needle and slid down over the needle into the patient's body using the needle to make the penetration and provide a guide to placement of the catheter, many intravenous catheters are of this type. This disclosure is related to yet another type, a catheter that is introduced into the patient through the bore of a sharp introducer needle. Through-the-needle catheters are further separated into two types by the introducer needle. When a through-the-needle catheter has a fixed hub for attachment of a fluid handling device, the introducer needle cannot be slid off the proximal end of the catheter. Catheters with fixed hubs either are used with a splitable introducer needle or the needle must be left on the catheter. One important application of catheters in medical practice is the use of long flexible catheters to introduce medicaments, often anesthetic or analgesic formulations, into the spine of a patient. In this application, the long (50–75 cm) flexible catheter tubing (generally 19–21 gauge) is introduced into the patient's epidural space through the bore of an introducer needle.

These spinal anesthesia procedures are widely used in hospital practice, with the generic name of "an epidural." As an example, the use of an epidural anesthetic is described in obstetric practice. The epidural anesthetic procedure is useful in many other types of procedures. In a typical obstetric procedure, the epidural catheter is often placed early in the patient's labor with the patient lying on her side, then the patient is placed on her back with the knees elevated for the rest of the delivery. Since the patient is on her back, the introducer needle generally must be removed. Most epidural catheters do not have fixed hubs thus allowing the introducer needle to be slid proximally off of the catheter and removed. Once the needle is removed, it is necessary to mount an adapter onto the catheter so that a fluid handling device such as a syringe may be attached to the catheter. The adapter is then often secured with tape onto the patient's body. The Tuohy-Borst adapter was developed for this application. The Tuohy-Borst adapter allows a fluid handling device with a male luer fitting to be mounted onto a small diameter (generally 19–21 gauge: Nominal Outside Diameters for these 19 to 21 gauges are between about 1.10 mm [19 gauge] to about 0.8mm [21 gauge] ) flexible catheter tube. The original Tuohy-Borst adapter is formed from metal and is considered reusable. Other variants of the original Tuohy-Borst are now available formed from thermoplastics. The thermoplastic adapters are generally supplied sterile and are considered single-use and disposable. The Tuohy-Borst type adapters all depend in some degree on a threaded collar being screwed down around the catheter to compress a resilient plug contained in a body portion. The seal around the catheter is formed by compressing the tip of the resilient plug into a cavity around the catheter tube by screwing the collar down onto the plug. In most of these adapters, it is easy for a practitioner to inadvertently over-tighten the threaded collar and occlude the catheter lumen. Alternatively, if the collar is not tightened down sufficiently, the adapter may leak or may even come off of the catheter tube. Most of the available adapters are generally cylindrical, may include a releasable latch mechanism and require at least about one-half rotation of the collar portion with respect to the body portion to secure the adapter onto the catheter.

A widely used adapter, available from B. Braun, Bethlehem, Pa., has a collar and a body portion. The Braun adapter is capable of almost four complete rotations of the collar with respect to the body portion from the initial engagement of the threads. Additionally, if this collar of the B. Braun adapter is fully unthreaded from the body portion, it may detach and allow disassembly of the adapter. Another widely used adapter is the disposable successor to the reusable Tuohy-Borst available from Becton Dickinson and Company, Franklin Lakes, N.J. The collar of this successor adapter is fully seated on the body after only about two and one half rotations of the collar with respect to the body. Additionally, unlike the B. Braun adapter, the collar is retained on the body when completely unthreaded so that it cannot easily fall off. Another available adapter, as disclosed in U.S. Pat. Nos. 5,053,015 and 5,226,898, has an external ratchet and includes small wings on both the body and the collar to facilitate the practitioners handling and, when the wings are aligned, provides some indication that the adapter is secured onto the tubing. When the adapter disclosed in the referenced patents is secured to the patient's body, the small wings may cause discomfort to the patient, and additionally, the adapter may sometimes be difficult for a gloved practitioner to handle.

Other than the catheter adapters disclosed in U.S. Pat. Nos. 5,053,015 and 5,226,898, substantially all of the available adapters do not provide the practitioner with much indication of the sufficiency of the degree of tightness of the collar with respect to the body, and it is not easily visually apparent if the collars are loosened so that the catheter tubing may be inserted into the adapter or if the collar is partially screwed down on the body, making it difficult to insert the catheter tube into the adapter body. Operating room time is expensive, and additionally, many procedures are conducted under time constraints that potentially have impact on the patient's well being. As a result, practitioners and their support staff make every effort to set up repeatable procedures with standardized placements of equipment to facilitate rapid implementation of procedures. If a practitioner attempts to put an adapter onto a catheter tube and has difficulty because the adapter is partially threaded, additional time is required. If a practitioner inadvertently over-tightens a collar of an adapter occluding the lumen, he may believe the catheter is clogged or kinked, remove it and have to repeat the placement. The repeat procedure not only subjects the patient to additional risk, but also significantly increases the time required. If an adapter is not sufficiently tightened, it may fall off or leak during an extended procedure, thereby resulting in improper patient medication. If a gloved practitioner has difficulty handling an adapter and drops it, there may be a time delay while another adapter is procured, and, in the case where the adapter is part of a procedure kit, another whole kit, with a significant cost increment, may need to be opened just to obtain another adapter. If an adapter were available that enabled a practitioner to simply insert the proximal end of the catheter into the adapter until it was fully seated, resulting in a substantially fluid tight connection and that required no further action of the practitioner other than to attach the desired fluid handling device, the art of attachment of fluid handling devices to catheters would be advanced. Such an adapter and a method for its use is disclosed hereinbelow.

SUMMARY

An adapter of the present invention useful for attaching a fluid handling device to a catheter includes a body having a proximal end, a distal end and an open passageway therethrough. The passageway includes a seat to receive the catheter and a cavity distal to the catheter seat. There is a gasket disposed in the cavity to form a substantially fluid tight seal about the catheter when the catheter is positioned on the catheter seat. The adapter further includes a retainer, disposed on the proximal end of the body over the gasket with an opening therethrough that is substantially aligned with the passageway. The opening is sufficient to allow the catheter to pass through into the passageway to engage the gasket and the catheter seat. The retainer has a plurality of flexible projections into the opening that are sized and shaped to engage the catheter and be proximally deflected by the placement of the catheter on the catheter seat. There is a rotatable collar disposed over the retainer on the distal end of the body, with an open port therethrough that is substantially aligned with the passageway to allow placement of the catheter into the passageway. The collar has a plurality of distal protuberances disposed to engage the flexible projections and to prevent distal flexion of the flexible projections on the retainer when the collar is in a first position with respect to the body thus to retain the catheter in the adapter for attachment to a fluid handling device. Additionally, the protuberances are disposed not to engage the flexible projections when the collar is rotated to a second position with respect to the body thereby to allow a distal flexion of the projections and a withdrawal of the catheter from the adapter.

The adapter of the invention provides practitioners with a simple and intuitive to use device. Unlike the current adapters, that require the practitioner to insert the proximal end of the catheter into the adapter, then tighten the threaded collar through several complete revolutions to achieve a fluid tight seal, a practitioner using the adapter of the invention simply inserts the proximal end of the catheter into the adapter, and proximally advances it until the proximal end of the catheter is positioned on the catheter seat. At that time the practitioner may attach the desired fluid handling device to the catheter for administration of the medicament. No further actions are necessary to achieve a substantially fluid tight seal.

BRIEF DESCRIPTION OF THE DRAWINGS

FIG. 5a is a cross-sectional view of the adapter of the invention taken from FIG. 1 along the line 5a—5a;

DETAILED DESCRIPTION

Figure 1:
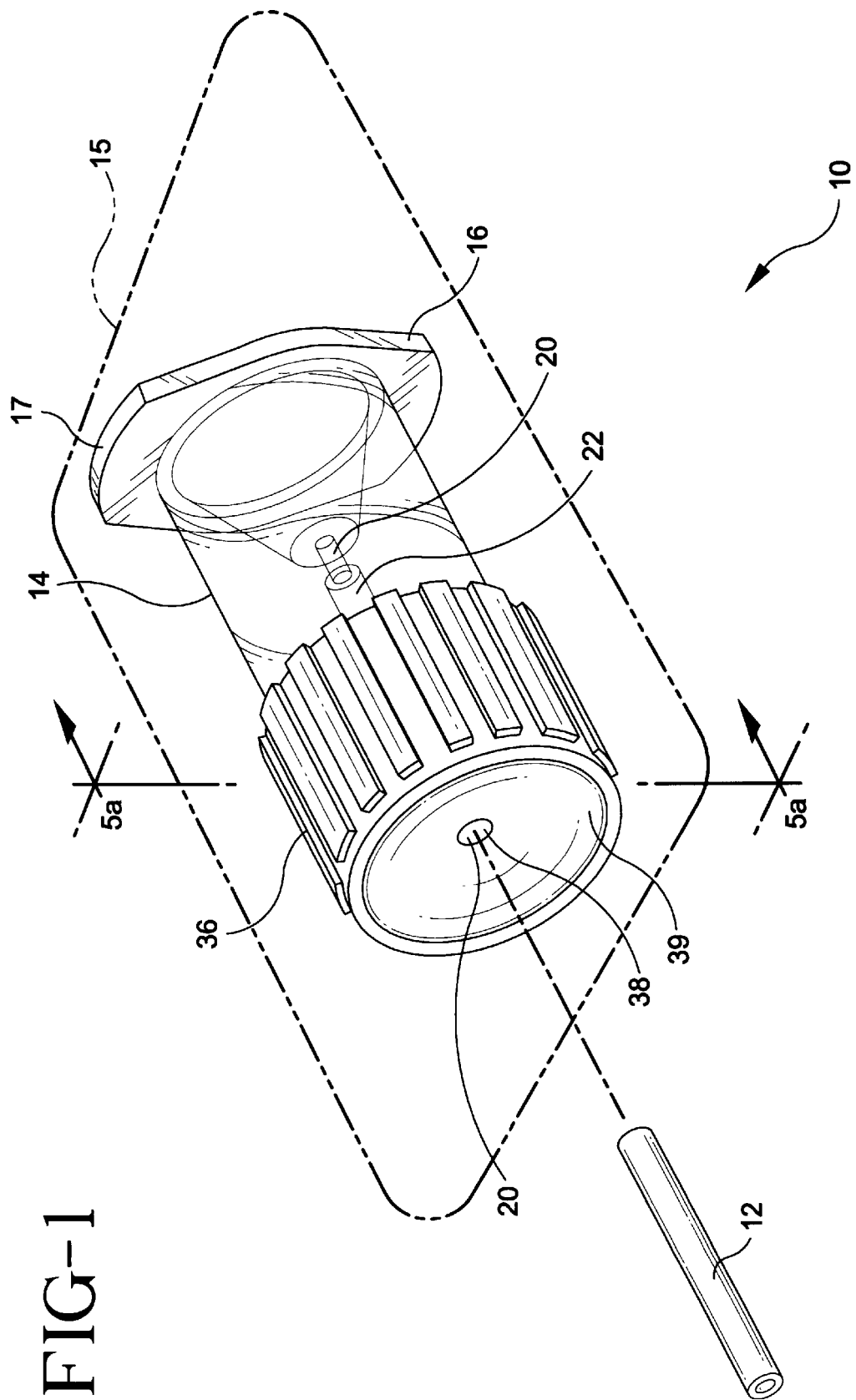
FIG. 1 is a perspective view of the adapter of the invention positioned to receive a catheter.
Figure 2:
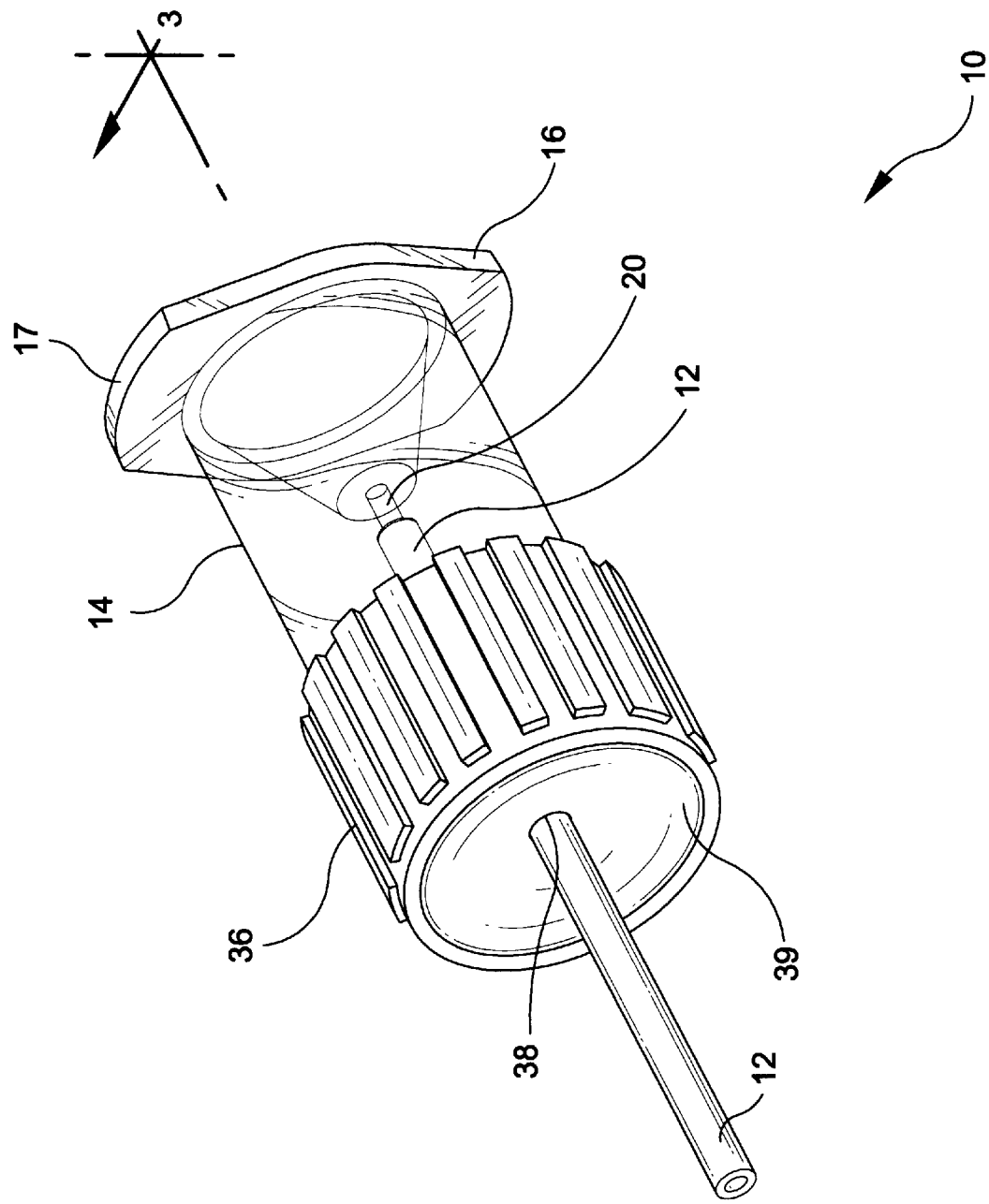
FIG. 2 is a perspective view of the adapter of FIG. 1 with the catheter positioned in the passageway.
Figure 3:
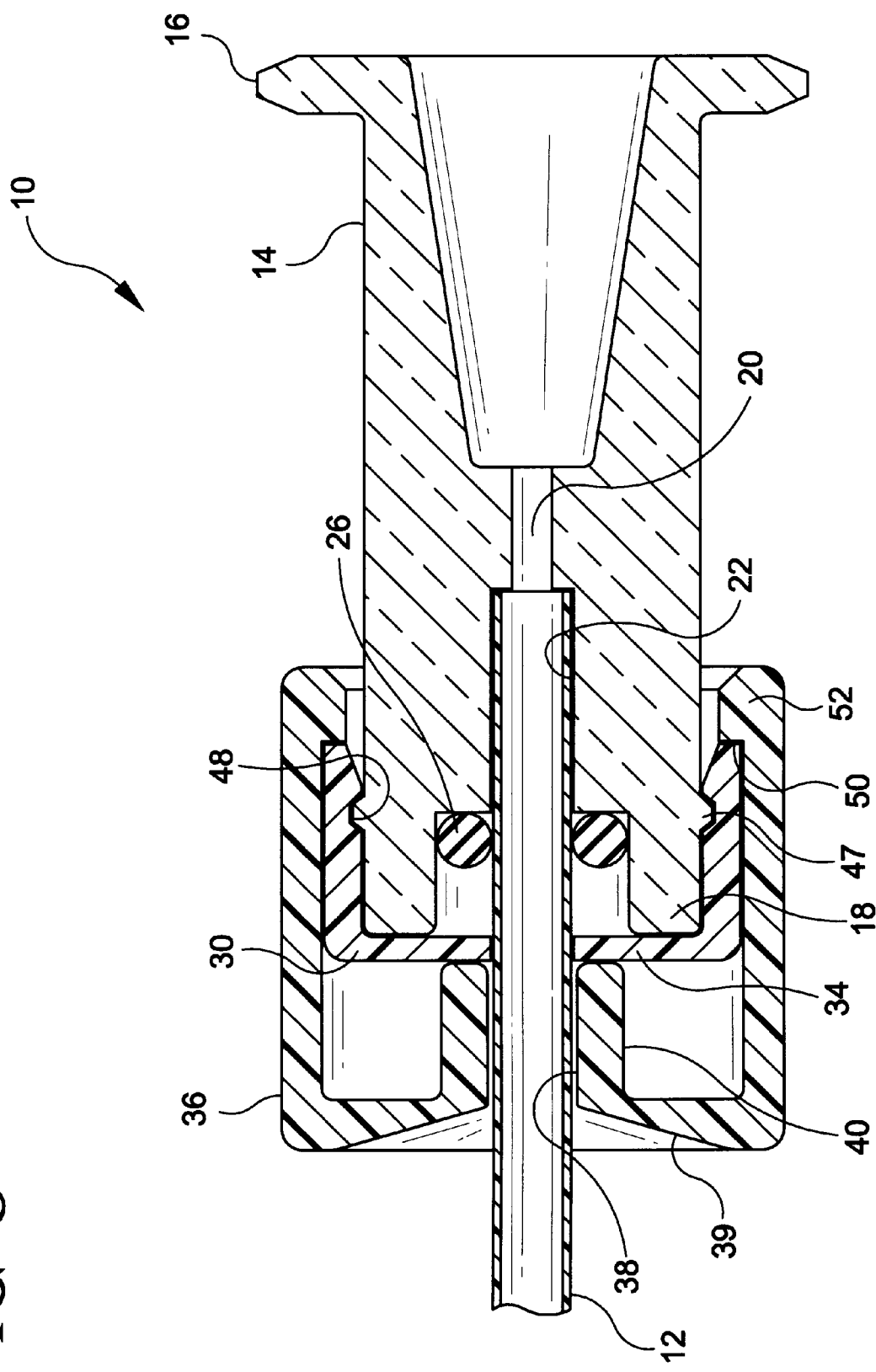
FIG. 3 is a cross-sectional view of the adapter of the invention taken from FIG. 2 along the line 3—3.
Figure 4:
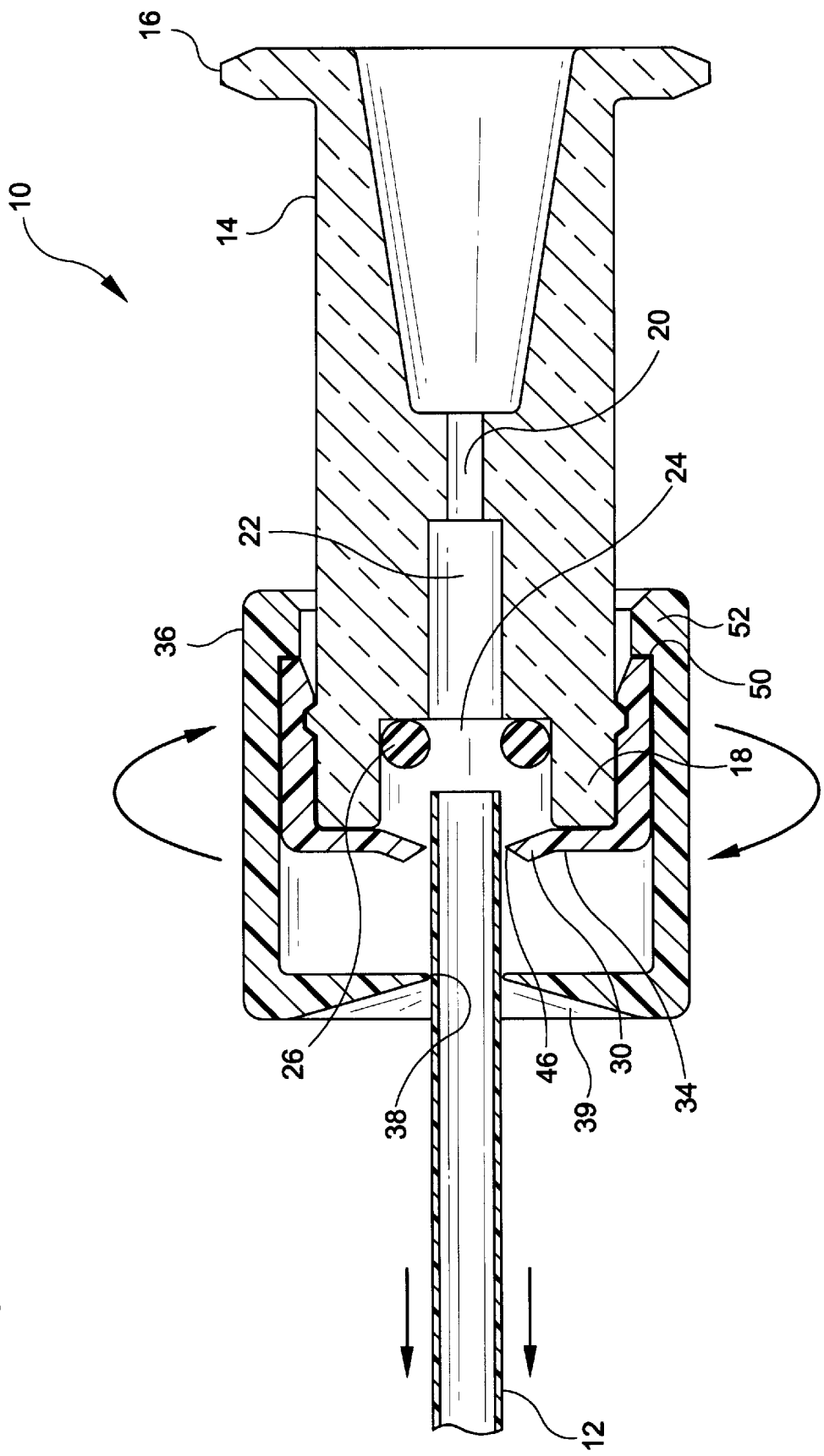
FIG. 4 is a cross-sectional view, analogous to the view of FIG. 3, of the adapter of the invention with the catheter partially withdrawn.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and their equivalents. In this disclosure, the term "proximal" refers to the portions of the device closest to the practitioner and the term "distal" refers to the portion of the device away from the practitioner.

Referring to FIGS. 1–5, an adapter 10 of the present invention useful for attaching a fluid handling device to a catheter 12 includes a body 14 having a proximal end 16, a distal end 18 and an open passageway 20 therethrough. Passageway 20 includes a seat 22 to receive catheter 12 and a cavity 24 distal to catheter seat 22. There is a gasket 26 disposed in cavity 24 to form a substantially fluid tight seal about catheter 12 when the catheter is positioned on catheter seat 22. Adapter 10 further includes a retainer 30, disposed on distal end 18 of body 14 over gasket 26 with an opening 32 therethrough that is substantially aligned with passageway 20. Opening 32 is sufficient to allow catheter 12 to pass through into passageway 20 to engage gasket 26 and catheter seat 22. Retainer 30 has a plurality of flexible projections 34 into opening 32 that are sized and shaped to engage catheter 12 and be proximally deflected by the placement of catheter 12 on catheter seat 22. There is a rotatable collar 36 disposed over retainer 30 on distal end 18 of body 14, with an open port 38 therethrough that is substantially aligned with passageway 20 to allow placement of catheter 12 into the passageway. Preferably, open port 38 has a tapered entrance area 39 to ease placement of catheter 12 into passageway 20 through port 38. Collar 36 has a plurality of proximal protuberances 40 disposed to engage flexible projections 34 and to prevent distal flexion of the flexible projections on retainer 30 when collar 36 is in a first position, best seen in FIG. 3, with respect to body 14 thus to retaining 12 catheter in adapter 10 for attachment to a fluid handling device. Additionally, protuberances 40 are disposed not to engage flexible projections 34 when collar 36 is rotated to a second position, best seen in FIGS. 4 and 5, with respect to body 14 thereby to allow a distal flexion of projections 34 and a withdrawal of catheter 12 from adapter 10.

Proximal end 16 preferably includes a female luer fitting 17 to facilitate attachment of a fluid handling device such as a syringe. Gasket 26 is preferably formed from a resilient elastomeric material. Suitable elastomeric materials include, but are not limited to, natural rubber, silicone elastomer, ethylene propylene diene monomer (EPDM) and the like.

Preferably, a material is selected with a Shore A durometer between about 45 and 70 formed into the shape of an "O" ring with an internal diameter and thickness suitable for forming a substantially fluid tight seal between the catheter and the adapter.

Figure 5A:
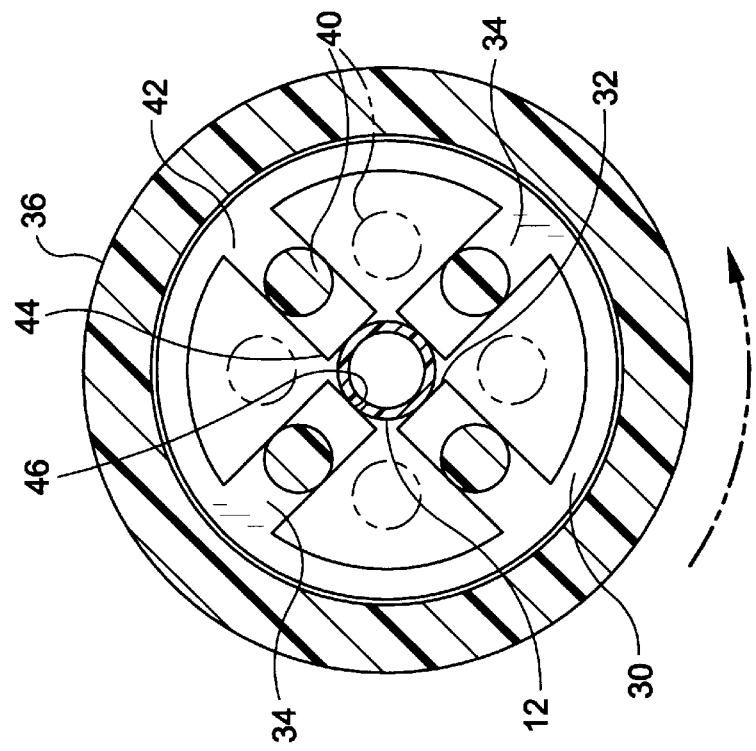
Figure 5B:
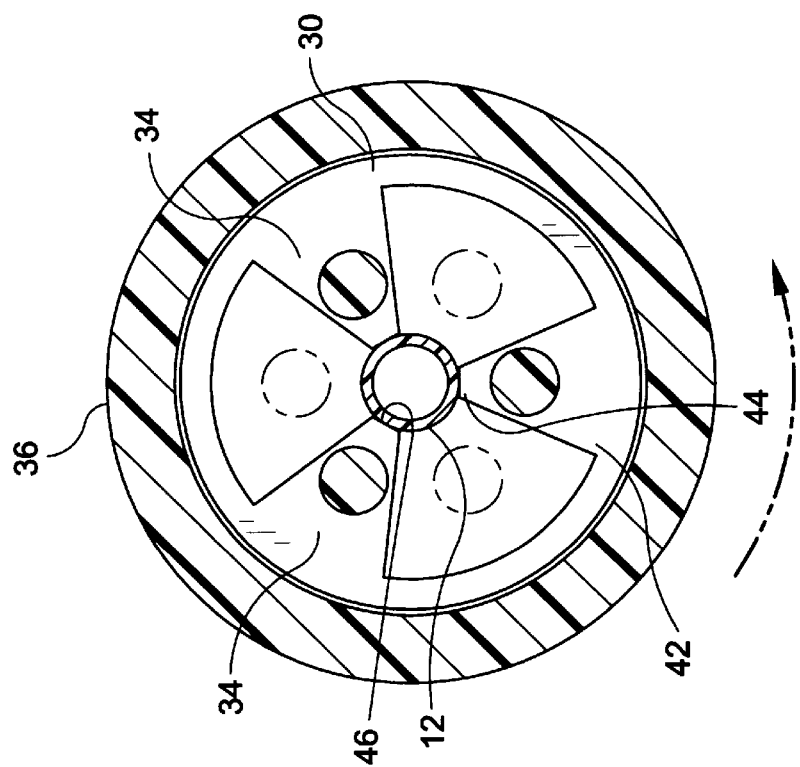
FIG. 5b, is a cross-sectional view of variant of the adapter of the invention, analogous to FIG. 5a, taken along the line 5b—5b.

Referring to FIGS. 5a and 5b, retainer 30 with the plurality of projections 34 may be formed from thermoplastic material or formed from a flexible metallic material, preferably with three or four projections 34. Projections 34 have an attached end 42 and a free end 44 that preferably is shaped into a sharp wedge shape 46 to engage catheter 12 when it is positioned into adapter 10. Projections 34 are sized and shaped so that they are flexed proximally and engage catheter 12 as the catheter is moved proximally to catheter seat 22, but do not penetrate the catheter wall or occlude the bore. Suitable materials for forming retainer 30 include, but are not limited to, thermoplastic materials such as polystyrene, polycarbonate, polypropylene, polyamide, polyacrylate, polyacetal, polysulfone and the like. Suitable metallic materials for forming retainer 30 include, but are not limited to, or any other flexible metallic material suitable for use in medical applications. When a metallic material is selected, retainer 30 may be formed by stamping, electromachining, edm or other metal working techniques suitable for forming thin flexible metal parts. Retainer 30 is preferably fixedly attached to body 14 by mechanical attachment including, but not limited to, the interaction of a projecting ring 47 and an annular groove 48 in retainer 30. Additionally, bonding techniques such as adhesive bonding, solvent bonding, heat staking and ultrasonic welding may be used, either by themselves or in combination with the mechanical attachment. Retainer 30 also defines a shoulder 50 that is sized and disposed to be engaged by a lip 52 on collar 36 to retain the collar on the body and allow for rotation of the collar with respect to the body.

Referring to FIGS. 3, 4, 5a and 5b, collar 36 has a number of proximal protuberances 40 disposed to engage a like number of projections 34 when collar 36 is in the first position with respect to body 14. Protuberances 40 are disposed to so that when collar 36 is rotated to the second position with respect to body 14, protuberances 40 do not engage projections 34 thereby allowing the projection to deflect proximally as catheter 12 is withdrawn distally from the adapter and release the catheter. In the case, as shown in FIG. 5b where there are three projections 34, collar 36 is rotated about one-sixth of a revolution with respect to body 14 to release the catheter. Similarly as shown in FIG. 5a, when there are four projections 34, collar 36 is rotated about one-eighth turn to disengage protuberances 40 from projections 34. Preferably, projections 34 and protuberances 40 are sized and shaped so that, once collar 36 is rotated from the first position to the second position with respect to body 14 thereby disengaging protuberances 40 from projections 34, projections 34 and protuberances 40 interfere with each other to substantially prevent rotation of the collar from the second position to the first position. This prevention of returning collar 36 to the first position, serves to substantially prevent adapter 10 from again being mounted onto a catheter and actively substantially prevents reuse of the adapter of the invention.

Body 14 is may formed from a thermoplastic material such as polystyrene, polypropylene, polycarbonate, polyamide, polyacrylate, polyacetal, polysulfone and the like. Preferably, body 14 is formed from a substantially transparent material so that when catheter 12 is positioned in passageway 20 on catheter seat 22, it is visible to the practitioner.

Preferably, adapter 10 is placed in a package 15, illustrated in phantom in FIG. 1, formed from materials substantially resistant to microorganisms, sealed in the package and exposed to agents that substantially render any microorganisms inside non-viable. Preferably, adapter 10 has collar 36 in the first position with respect to body 14 when placed in package 15 so that the adapter is ready for use as soon as the package is opened. Suitable materials for forming package 15 include, but are not limited to paper, non-wovens, thermoplastic films, metallic foils and composites of these materials. Suitable agents for rendering the microorganisms non-viable include, but are not limited to, ethylene oxide, ionizing radiation and the like. When materials are selected for forming adapter 10 and package 15, consideration should be given to the sterilization conditions to ensure materials compatibility.

A method for mounting adapter 10 onto a catheter 12 includes orienting catheter 12 with distal open port 38 and proximally advancing catheter 12 until the proximal end of the catheter is seated on catheter seat 22. Adapter 10 is now ready for the practitioner to attach a suitable fluid handling device.

Figure 6:
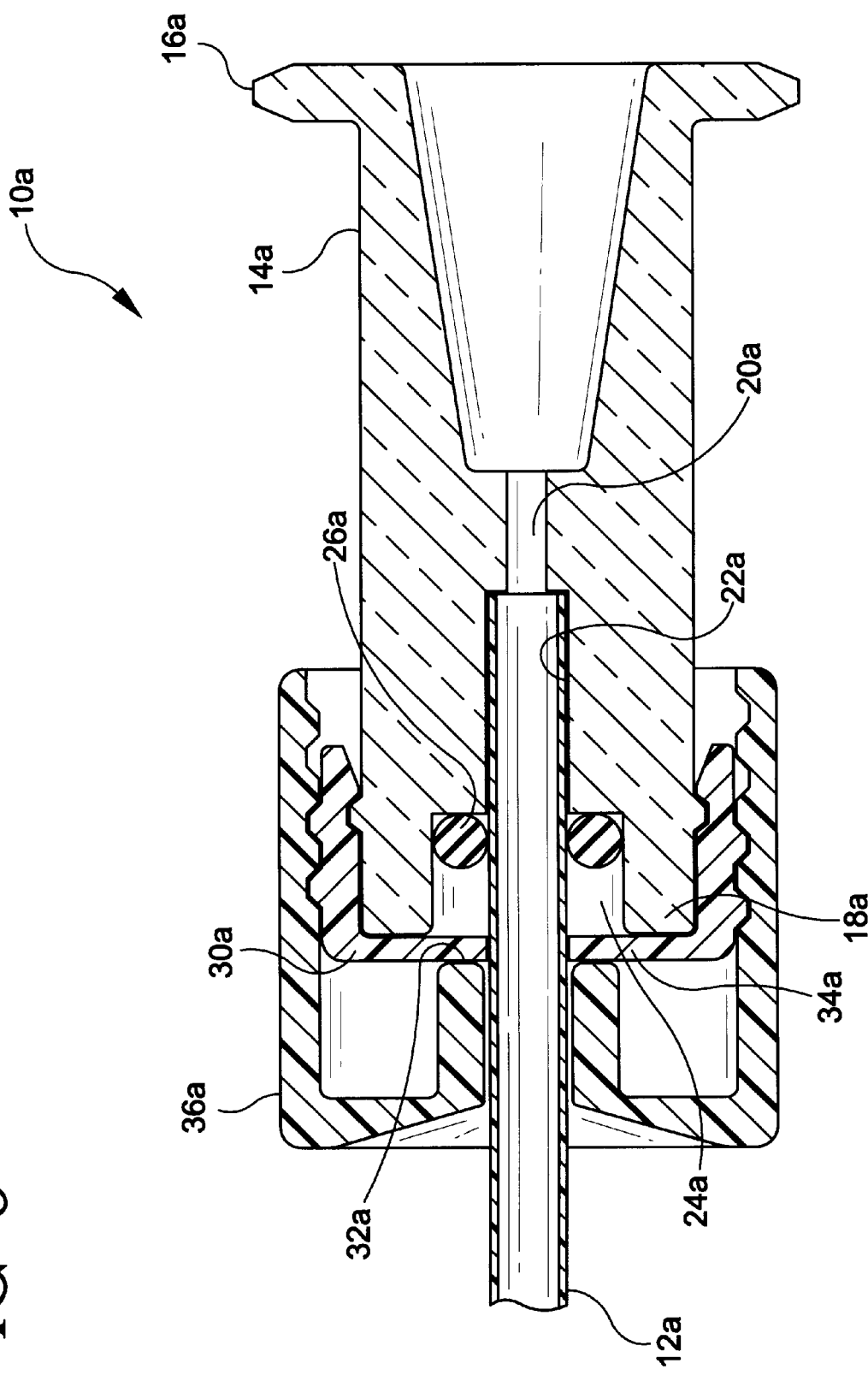
FIG. 6 is a longitudinal cross-sectional view, analogous to FIG. 3, of an alternate embodiment of the adapter of the invention.
Figure 7:
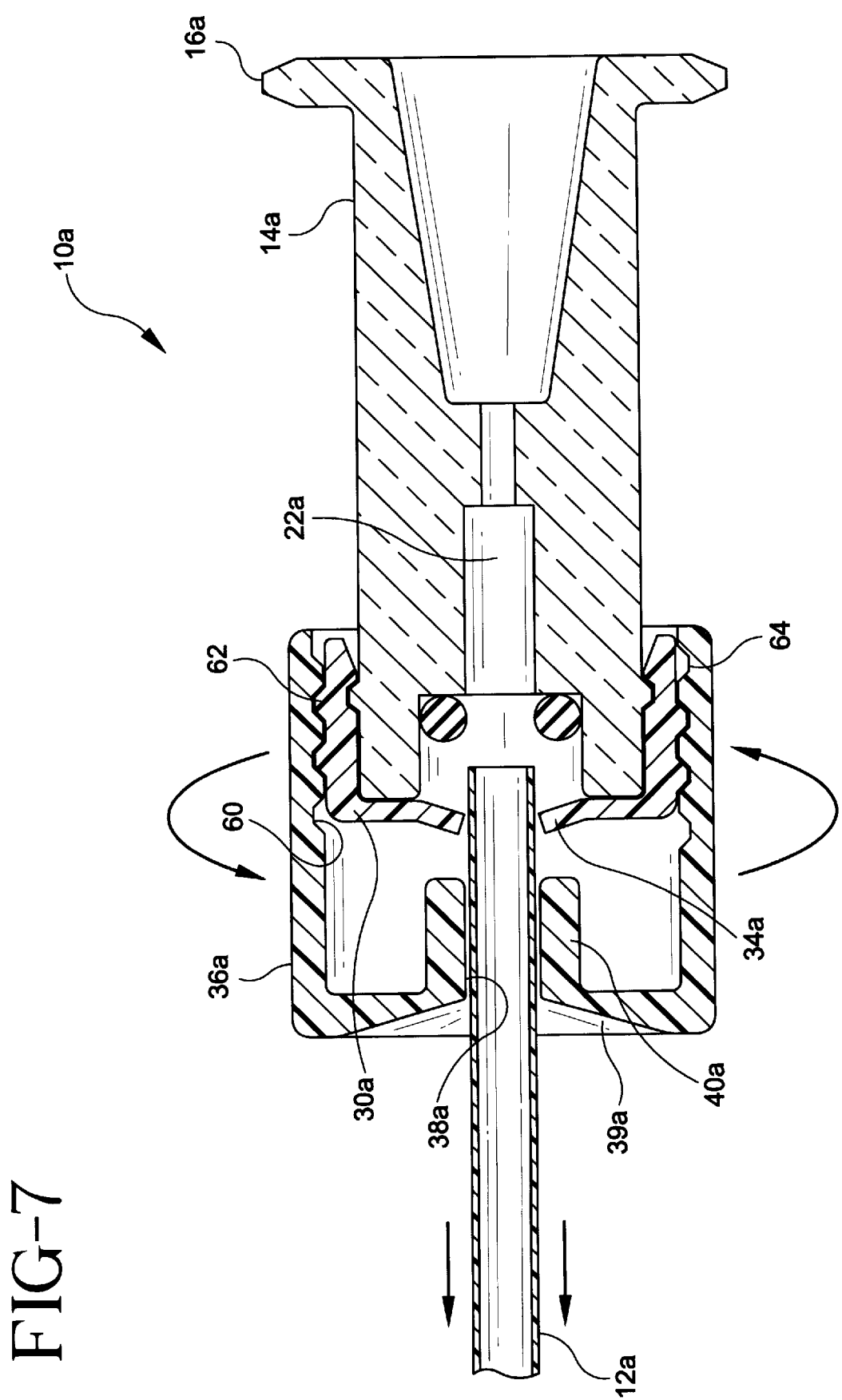
FIG. 7 is a longitudinal cross-sectional view, analogous to FIG. 4, of the adapter shown in FIG. 6, with the catheter partially withdrawn.
Figure 8:
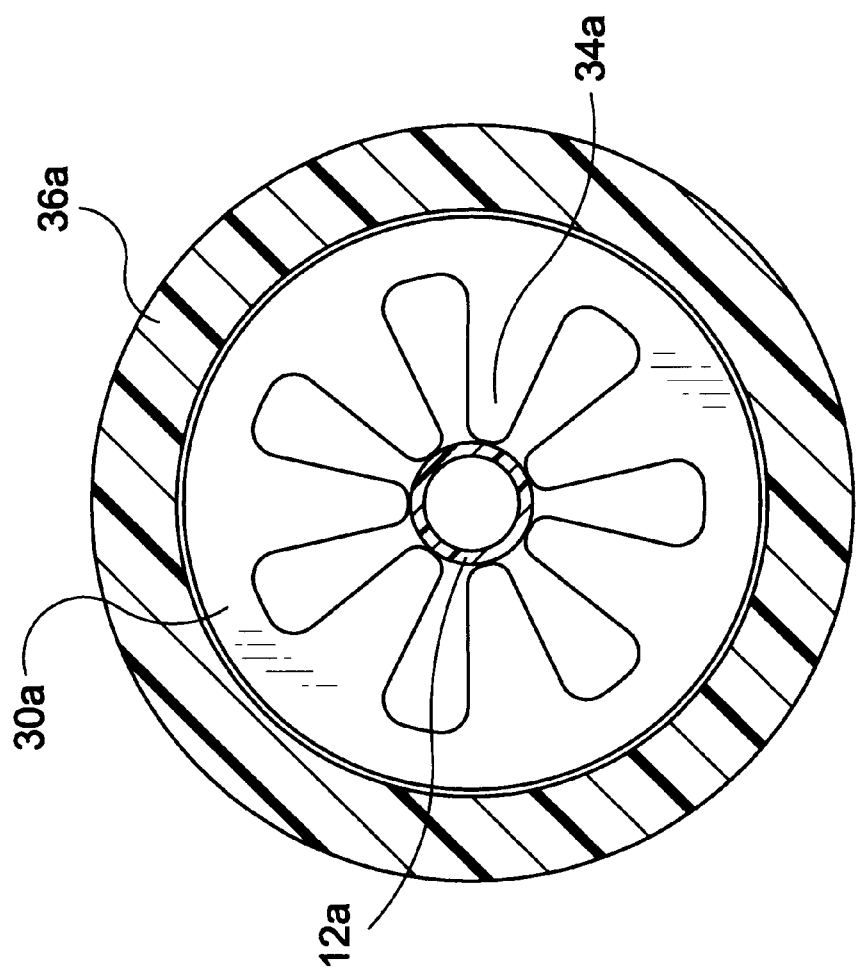
FIG. 8, is a cross-sectional view, analogous to FIGS. 5a and 5b, of the adapter of FIGS. 6 and 7.

Referring to FIGS. 6, 7 and 8, an alternate embodiment to the adapter is shown that is similar to the cross-sectional views of the adapter illustrated in FIGS. 3, 4, 5a and 5b. In this embodiment, there are elements similar in structure and function to the embodiment of the present invention shown in FIGS. 1–5b. Accordingly, substantially similar components that perform substantially similar functions are numbered identically to those components of the embodiment of FIGS. 1–5b except that a suffix "a" is added to identify those components in FIGS. 6, 7 and 8.

Referring to FIGS. 6, 7 and 8, an adapter 10a of the present invention useful for attaching a fluid handling device to a catheter 12a includes a body 14a having a proximal end 16a, a distal end 18a and an open passageway 20a therethrough. Passageway 20a includes a seat 22a to receive catheter 12a and a cavity 24a proximal to catheter seat 22a. There is a gasket 26a disposed in cavity 24a to form a substantially fluid tight seal about catheter 12a when the catheter is positioned on catheter seat 22a. Adapter 10a further includes a retainer 30a, disposed on distal end 18a of body 14a over gasket 26a with an opening 32a therethrough that is substantially aligned with passageway 20a. Opening 32a is sufficient to allow catheter 12a to pass through into passageway 20a to engage gasket 26a and catheter seat 22a. Retainer 30a has a plurality of flexible projections 34a into opening 32a that are sized and shaped to engage catheter 12a and be proximally deflected by the placement of catheter 12a on catheter seat 22a. There is a rotatable collar 36a disposed over retainer 30a on distal end 18a of body 14a, with an open port 38a therethrough that is substantially aligned with passageway 20a to allow placement of catheter 12a into the passageway. Preferably, open port 38a has a tapered entrance area 39a to ease placement of catheter 12a into passageway 20a through port 38a. Collar 36a has a proximal protuberance 40a, in this embodiment preferably in the form of a cylinder, disposed to engage flexible projections 34a, best seen in FIG. 8, and to prevent distal flexion of the flexible projections on retainer 30a when collar 36a is in a first position, best seen in FIG. 6, with respect to body 14a thus to retaining catheter 12a in adapter 10a for attachment to a fluid handling device. Additionally, protuberance 40a is disposed not to engage flexible projections 34a by distally withdrawing collar 36a away from retainer 30a as collar 36a rotated to a second position, best seen in FIG. 7, thereby to allow a distal flexion of projections 34a and a withdrawal of catheter 12 from adapter 10. In this embodiment, collar 36a includes a female thread 60 and retainer 30a includes a male thread 62. Preferably, threads 60 and 62 include a stop 64 to prevent collar 36a from being rotated more than an amount sufficient to substantially eliminate contact between distal protuberance 40a and projections 34a. Stop 64 preferably is sized and shaped so that a force for rotation between the first position and the second position is substantially less than a force for rotation between the second position and the first position, thereby substantially preventing inadvertent reuse of the adapter.

The invention provides practitioners with an easy-to-use adapter for attaching a fluid handling device to a catheter. The adapter of the invention does not require as much manipulation to mount as previous adapters, is readily and intuitively dismounted and, substantially prevents inadvertent reuse

What is claimed is:

1. An adapter for attaching a fluid handling device to a catheter comprising:
    a body having a proximal end, a distal end and an open passageway therethrough, said passageway including a seat to receive the catheter and a cavity distal to said catheter seat;
    a gasket disposed in said cavity to form a substantially fluid tight seal about the catheter when the catheter is positioned on said catheter seat;
    a retainer, disposed on the distal end of the body over said gasket, said retainer having an opening therethrough substantially aligned with said passageway sufficient to allow the catheter to pass through into said passageway to engage said gasket and said catheter seat, said retainer having a plurality of flexible projections into said opening being sized and shaped to engage the catheter and be proximally deflected by the placement of the catheter on said catheter seat; and
    a rotatable collar disposed over said retainer on said distal end of said body, said collar having an open port therethrough substantially aligned with said passageway to allow placement of the catheter into said passageway, said collar having a plurality of proximal protuberances disposed to engage said flexible projections and to prevent distal flexion of said flexible projections on said retainer when said collar is in a first position with respect to said body thereby to retain the catheter in said adapter for attachment to a fluid handling device, whereby said protuberances being disposed not to engage said flexible projections when said collar is rotated to a second position with respect to said body thereby to allow a distal flexion of said projections and withdrawal of the catheter from said adapter.

2. The adapter of claim 1 wherein said proximal end of said body further includes a female luer fitting to attach said adapter to the fluid handling device.

3. The adapter of claim 1 wherein said gasket is formed from a resilient elastomeric material.

4. The adapter of claim 3 wherein said resilient elastomeric material has a durometer between about Shore A 45 and 70 and is selected from the group consisting of natural rubber, silicone elastomer and ethylene propylene diene monomer (EPDM).

5. The adapter of claim 4 wherein said resilient elastomeric material is shaped into the form of an "O" ring.

6. The adapter of claim 1 wherein said retainer has four projections substantially equally arranged about said opening.

7. The adapter of claim 1 wherein said retainer has three projections substantially equally arranged about said opening.

8. The adapter of claim 1 wherein said projections on said retainer each have an attached end and a free end that projects into said opening in said retainer, said free ends each comprising a sharp wedge disposed to engage the catheter when the catheter is placed into said passageway onto said catheter seat, so that a force for insertion of the catheter into the passageway and onto said catheter seat is less than a force for withdrawal of the catheter from the passageway when said collar is in said first position.

9. The adapter of claim 1 wherein said body is formed from a thermoplastic material selected from the group consisting of polystyrene, polypropylene, polycarbonate, polyamide, polyacrylate, polyacetal and polysulfone.

10. The adapter of claim 1 wherein said body is formed from a substantially transparent material so that a practitioner can observe proper placement of the catheter on said catheter seat.

11. The adapter of claim 1 wherein said retainer is formed from a thermoplastic material selected from the group consisting of polystyrene, polycarbonate, polypropylene, polyamide, polyacrylate, polyacetal and polysulfone.

12. The adapter of claim 1 wherein said retainer is formed from a metallic material selected from the group consisting of stainless steel, beryllium copper alloys and titanium alloys.

13. The adapter of claim 1 wherein said collar is formed from a material selected from the group consisting of polystyrene, polycarbonate, polypropylene, polyamide, polyacrylate, polyacetal and polysulfone.

14. The adapter of claim 1 wherein said body portion and said collar each include conjugate threads and said rotation of said collar from said first position to said second position causes a distal movement of said collar with respect to said body thereby withdrawing said protuberances from said projections.

15. The adapter of claim 1 wherein said projections on said retainer are substantially uniformly spaced apart thereby leaving void areas between said projections and wherein said protuberances on said collar are disposed so that said protuberances engage said projections when said collar is in said first position with respect to said body and are disposed so that said protuberances are positioned into said void areas when said collar is rotated to said second position.

16. The adapter of claim 1 wherein said projections and said protuberances are sized and shaped so that when said collar is moved from said first position to said second position, said protuberances and said projections are disposed to substantially prevent movement of said collar from said second position to said first position thereby rendering said adapter incapable attachment onto a catheter and substantially preventing reuse of said adapter.

17. An adapter for attaching a fluid handling device to a catheter comprising:
    a body having a proximal end, a distal end and an open passageway therethrough, said passageway including a seat to receive the catheter and a cavity distal to said catheter seat;
    a gasket disposed in said cavity to form a substantially fluid tight seal about the catheter when the catheter is positioned on said catheter seat;
    a retainer, disposed on the distal end of the body over said gasket, said retainer having an opening therethrough substantially aligned with said passageway sufficient to allow the catheter to pass through into said passageway to engage said gasket and said catheter seat, said retainer having four flexible projections into said opening being sized and shaped to engage the catheter and be proximally deflected by the placement of the catheter on said catheter seat; said projections on said retainer each having an attached end and a free end comprising a sharp wedge that projects into said opening in said retainer and disposed to engage the catheter when the catheter is placed into said passageway onto said catheter seat;

a rotatable collar disposed over said retainer on said distal end of said body, said collar having an open port therethrough substantially aligned with said passageway to allow placement of the catheter into said passageway, said collar having a plurality of proximal protuberances disposed to engage said flexible projections and to prevent distal flexion of said flexible projections on said retainer when said collar is in a first position with respect to said body thereby to retain the catheter in said adapter for attachment to a fluid handling device, whereby said protuberances being disposed not to engage said flexible projections when said collar is rotated to a second position with respect to said body thereby to allow a distal flexion of said projections and a withdrawal of the catheter from said adapter.

18. A method for attaching an adapter useful for attachment of a fluid handling device to a catheter comprises:

providing an adapter including a body having a proximal end, a distal end and an open passageway therethrough, said passageway including a seat to receive the catheter, and a cavity distal to said catheter seat;

a gasket disposed in said cavity to form a substantially fluid tight seal about the catheter when the catheter is positioned on said catheter seat;

a retainer, disposed on the distal end of the body over said gasket, said retainer having an opening therethrough substantially aligned with said passageway sufficient to allow the catheter to pass through to engage said gasket and said catheter seat, said retainer having a plurality of flexible projections into said opening being sized and shaped to engage the catheter and be proximally deflected by the placement of the catheter on said catheter seat; and a rotatable collar disposed over said retainer on said distal end of said body, said collar having an open port therethrough substantially aligned with said passageway to allow placement of the catheter into the passageway, said collar having a plurality of proximal protuberances disposed to engage said flexible projections and to prevent distal flexion of said flexible projections on said retainer when said collar is in a first position with respect to said body thereby to retain the catheter in said adapter for attachment to a fluid handling device, whereby said protuberances being disposed not to engage said flexible projections when said collar is rotated to a second position with respect to said body thereby to allow a distal flexion of said projections and a withdrawal of the catheter from said adapter, wherein said collar is in said first position with respect to said body;

inserting a proximal end of a catheter into said passageway through said port in said collar; and advancing the end of the catheter proximally until the proximal end of the catheter is positioned on said catheter seat, thereby attaching said adapter to the catheter.

\* \* \* \* \*